(12) United States Patent
Hancock et al.

(10) Patent No.: US 10,932,843 B2
(45) Date of Patent: Mar. 2, 2021

(54) ELECTROSURGICAL SNARE

(71) Applicant: CREO MEDICAL LIMITED, Monmouthshire (GB)

(72) Inventors: Christopher Paul Hancock, Bath (GB); Malcolm White, Monmouthshire (GB); Craig Gulliford, Monmouthshire (GB); Brian Saunders, Rickmansworth (GB); Sandra May Bernadette Holmes, Stevenage (GB)

(73) Assignee: CREO MEDICAL LIMITED, Chepstow (GB)

( * ) Notice: Subject to any disclaimer, the term of this patent is extended or adjusted under 35 U.S.C. 154(b) by 866 days.

(21) Appl. No.: 14/904,417

(22) PCT Filed: Jun. 26, 2014

(86) PCT No.: PCT/GB2014/051957
§ 371 (c)(1),
(2) Date: Jan. 11, 2016

(87) PCT Pub. No.: WO2015/004420
PCT Pub. Date: Jan. 15, 2015

(65) Prior Publication Data
US 2016/0166314 A1    Jun. 16, 2016

(30) Foreign Application Priority Data

Jul. 11, 2013 (GB) .................... 1312416

(51) Int. Cl.
*A61B 18/14* (2006.01)
*A61B 17/3205* (2006.01)
(Continued)

(52) U.S. Cl.
CPC ........ *A61B 18/1402* (2013.01); *A61B 17/221* (2013.01); *A61B 17/32056* (2013.01);
(Continued)

(58) Field of Classification Search
CPC .......... A61B 17/221; A61B 2017/2212; A61B 17/32056; A61B 18/1402;
(Continued)

(56) References Cited

U.S. PATENT DOCUMENTS 4,905,691 A * 3/1990 Rydell .................. A61B 18/14
606/47
2009/0131926 A1* 5/2009 Rusin ..................... A61B 18/18
606/33
(Continued)

FOREIGN PATENT DOCUMENTS

EP    0 150 253 A2    8/1985
EP    2 052 669 A1    4/2009
(Continued)

OTHER PUBLICATIONS

Japanese Office Action of related Japanese Patent Application No. 2016-524888 dated Mar. 20, 2018.
(Continued)

*Primary Examiner* — Ronald Hupczey, Jr.
(74) *Attorney, Agent, or Firm* — Arent Fox LLP

(57) ABSTRACT

An electrosurgical snare, e.g. suitably sized for insertion down the instrument channel of an endoscope, arranged to radiate microwave frequency energy (e.g. having a frequency greater than 1 GHz) from an elongate conductive element within an area encircled by a retractable loop. The elongate conductive element and retractable loop may be independently slidable relative to a snare base at a distal end of a sleeve to provide an appropriate device configuration. By controlling the shape of the emitted microwave field, the risk of collateral thermal damage can be reduced.

16 Claims, 9 Drawing Sheets

(51) Int. Cl.
  *A61B 18/18* (2006.01)
  *A61B 17/221* (2006.01)
  *A61B 18/00* (2006.01)

(52) U.S. Cl.
  CPC .. *A61B 18/1815* (2013.01); *A61B 2017/2212* (2013.01); *A61B 2018/00494* (2013.01); *A61B 2018/00589* (2013.01); *A61B 2018/00607* (2013.01); *A61B 2018/00875* (2013.01); *A61B 2018/141* (2013.01); *A61B 2018/144* (2013.01); *A61B 2018/1407* (2013.01); *A61B 2018/1853* (2013.01); *A61B 2018/1861* (2013.01)

(58) Field of Classification Search
  CPC ........ A61B 2018/141; A61B 2018/144; A61B 18/18; A61B 18/1815; A61B 2018/1853; A61B 2018/1861; A61B 2018/1407; A61B 2018/183
  USPC .......................................................... 606/33
  See application file for complete search history.

(56) References Cited

U.S. PATENT DOCUMENTS

| | | | |
|---|---|---|---|
| 2009/0295674 A1* | 12/2009 | Bonn | A61B 18/18 343/872 |
| 2010/0121319 A1 | 5/2010 | Chu et al. | |
| 2010/0137857 A1 | 6/2010 | Shroff et al. | |
| 2012/0172864 A1 | 7/2012 | Farin et al. | |
| 2013/0023871 A1 | 1/2013 | Collins | |
| 2013/0041362 A1* | 2/2013 | Lee | A61B 18/1815 606/33 |

FOREIGN PATENT DOCUMENTS

| | | |
|---|---|---|
| EP | 2 742 893 A1 | 6/2014 |
| GB | 2472012 A | 1/2011 |
| JP | H11-19091 A | 1/1999 |
| JP | 2008-206994 A | 9/2008 |
| JP | 2012-508062 A | 4/2012 |
| JP | 2012-506300 A | 8/2012 |
| WO | WO 2010/048335 A1 | 4/2010 |

OTHER PUBLICATIONS

British Search and Examination Report of related British patent application No. GB1411391.4 dated Jan. 28, 2015.
British Search Report of related British patent application No. GB1312416.9 dated Dec. 23, 2013.
International Search Report and Written Opinion of PCT/GB2014/051957 dated Feb. 9, 2014.

\* cited by examiner

ELECTROSURGICAL SNARE

CROSS-REFERENCE TO RELATED APPLICATION

This application is a National Stage entry of International Application No. PCT/GB2014/051957, filed Jun. 26, 2014, which claims priority to United Kingdom Patent Application No. 13124146.9, filed Jul. 11, 2013. The disclosures of the priority applications are incorporated in their entirety herein by reference.

FIELD OF THE INVENTION

The invention relates to a surgical snare, e.g. for use in a polypectomy procedure. In particular, the invention may be concerned with medical snares suitable for insertion down the instrument channel of an endoscope (or any other type of scoping device used in the gastrointestinal (GI) tract or elsewhere in the human or animal body), and which include a means for introducing electromagnetic energy into biological tissue.

BACKGROUND TO THE INVENTION

Polyps in the GI tract can be removed using a medical snare in an endoscopic procedure, e.g. using a colonoscope. In the case of pedunculated polyps, the snare is passed over the polyp and tightened around the polyp's neck, which is then cut and the polyp removed. The cutting process may be performed or enhanced by passing a radiofrequency (RF) current through the biological tissue. The current may also facilitate cauterization.

Sessile polyps can be removed in a similar manner. It is preferable to "plump up" such polyps before removal by injecting saline or sodium hyaluronate, under the polyp to raise it away from the surrounding colon wall. This may help to reduce the risk of bowel perforation.

It is known to incorporate electrodes into the loop of a snare in order to provide an integrated means for delivering the RF current. Both monopolar, for use with a separate ground pad attached to the patient, and bipolar arrangements are known.

A disadvantage of known RF cutting snares is the high level of electrical power (in particular the use of high voltages) needed to initiate cutting action, as it carries with it the risk of unwanted thermal damage to the bowel wall. For example, the peak voltage associated with monopolar and bipolar coagulation may be in excess of 4,500 V and 450 V respectively.

SUMMARY OF THE INVENTION

At its most general, the present invention proposes snare structures arranged to radiate microwave frequency energy (e.g. electromagnetic energy with a frequency of at least three orders of magnitude higher than typical RF energy) within the area encircled by the snare's loop. By controlling the shape of the emitted microwave field, the risk of collateral thermal damage can be reduced. For example, typical peak voltages in embodiments of the invention are 10 V or less. Moreover, the emitted microwave field can be more effective than an RF field at coagulating blood.

According to a first aspect of the invention there is provided a surgical snare comprising: a retractable loop of conductive material for encircling an area containing biological tissue; a radiating structure arranged to radiate microwave frequency energy into the area encircled by the retractable loop; and a coaxial cable for conveying microwave frequency energy to the radiating structure, the coaxial cable comprising an inner conductor, an outer conductor surrounding and coaxial with the inner conductor, and a dielectric material separating the inner conductor and the outer conductor, wherein the radiating structure comprises: an elongate conductive member connected to the inner conductor of the coaxial cable and being electrically insulated from the outer conductor of the coaxial cable, and a snare base at a distal end for the coaxial cable, the snare base having a feed channel for conveying a length of the conductive material that forms the retractable loop, wherein the elongate conductive member comprises a distal portion that protrudes into the area encircled by the retractable loop to act as a radiating microwave monopole antenna, and a proximal portion that extends through the snare base alongside the feed channel. With this radiating structure, microwave power may be launched into the area encircled by the retractable loop both via the radiating microwave monopole antenna and also via a travelling wave set up on the conductive material by coupling energy from the proximal portion of the elongate conductive element into the length of conductive material in feed channel. Thus, the radiated microwave field may be directed into biological tissue held by the snare. The snare base may comprise a pair of feed channels, each feed channel receiving a length of the conductive material that forms the retractable loop, e.g. on opposite side of the elongate conductive member.

The electrical length of the elongate conductive member may be about $$\frac{(2n-1)\lambda_L}{4},$$

where $\lambda_L$ is the wavelength of the microwave frequency energy along the proximal portion of the elongate conductive element, i.e. the wavelength in the snare base, and n is a positive integer.

The snare base may comprise a plastic or dielectric casing that can be shaped to prevent the biological tissue held by the snare from being forced down over the elongate conductive element. The snare base may include other dielectric components, e.g. for controlling the position of the snare or for permitting limited penetration of the elongate conductive element into the biological tissue.

Herein, "microwave frequency" may be used broadly to indicate a frequency range of 400 MHz to 100 GHz, but preferably the range 1 GHz to 60 GHz, more preferably 2.45 GHz to 30 GHz or 5 GHz to 30 GHz. Specific frequencies that have been considered are: 915 MHz, 2.45 GHz, 3.3 GHz, 5.8 GHz, 10 GHz, 14.5 GHz and 24 GHz.

The surgical snare of the invention may be configured for insertion down an instrument channel of an endoscope, or may be arranged for use in laparoscopic surgery or in a NOTES procedure.

One advantage of using microwave frequency energy is that the depth of penetration of the electric field into biological tissue is small, e.g. of the order of millimeters at the frequency of choice. The focused heat profile depends on the square of the electric field, and the conductivity, density and specific heat capacity of the target tissue being treated. The microwave field emitted by the radiating microwave monopole antenna is therefore naturally confined to biological tissue in the region of the snare, thereby reducing the risk of collateral thermal damage.

The microwave frequency energy in the invention may be for the purpose of coagulating blood, i.e. sealing blood vessels, in the tissue encircled by the snare, to assist in the overall removal process. The stem of the polyp may be cut by the action of the retractable loop, i.e. the conductive material of the loop may comprise a sharp wire or the like. Alternatively or additionally, a blade or other cutting structure may be formed on the snare base, whereby drawing the biological tissue towards the snare base by closing the loop causes cutting.

In another embodiment, the snare may be configured to receive both RF and microwave frequency energy. The snare may operate as a conventional bipolar RF device to cut through the stalk, but with the added ability to switch in the microwave frequency energy when coagulation is required. In this configuration, the conductive material of the retractable loop may comprise two conductors separated by an insulator to deliver a local RF field. One or both of the same conductors may be used to deliver the microwave energy. The spacing between the two conductors is preferably 0.5 mm or less and the diameter or width of the conductors is preferably 1.5 mm or less to form a practically useful device. The conductors may be arranged in a co-planar configuration, where the active and the return are on the same surface or both surfaces and/or a configuration where electrodes are deposited onto a dielectric may be employed where the active and return conductors alternate along the length of the loop.

The retractable loop may not be conductive along its whole length. It may be desirable to use a non-metallic, e.g. nylon, loop to snare and assist with cutting through the stalk. The radiating structure may be configured to operate only in a region at the snare base, i.e. at the "neck" of the snare. In this configuration, microwave energy may also assist with the mechanical cut. In one arrangement, the radiating neck may take the form of a 'V' and in another, the radiating section (e.g. comprising a conductive section or coating on the loop) may form a part of the circumference of the loop, i.e. 45°, 90° or 180°.

Preferably, the length of the elongate conductive member and in particular the length of proximal portion thereof is determined by modeling because of the complicated and non-uniform structure surrounding it at the neck of the snare, based on the microwave frequency to be used.

If the snare is non-conductive, the elongate conductive member may be shaped to penetrate biological tissue. It may have a pointed distal end. It may be coated in a biocompatible material, e.g. PTFE or similar. Thus, the microwave frequency energy may be primarily radiated into blood. The dielectric properties of blood may thus be used to determine the properties of the radiating structure. For example, the relative permittivity (dielectric constant) $\varepsilon_r$ of blood at a frequency of 5.8 GHz is 52.539. The loaded wavelength $\lambda_L$ in this case may thus be 7.25 mm. In general, the formula for calculating $\lambda_L$ in a medium whose relative permittivity is $\varepsilon_r$ is $$\lambda_L = \frac{c}{f\sqrt{\varepsilon_r}},$$

where c is the speed of light and f is the microwave frequency. The length of the elongate conductive member may in this be close to any one of 1.81 mm, 5.44 mm, or 9.06 mm, which are all odd multiples of a quarter loaded wavelength. Ideally the length may be greater than 1 mm and less than 6 mm. This range of lengths is commensurate with the size of the polyp structure that may be encountered in a polypectomy.

The coaxial cable may be encased in a sleeve suitable for insertion through the instrument channel of an endoscope. The coaxial cable may extend between a proximal end, e.g. having a microwave connector for connecting to a suitable microwave signal generator, and a distal end at which the radiating structure is located. The length of the coaxial cable may be suitable for endoscopic procedures, e.g. 2 m or more. The snare base may include an insulating cap at its distal end to ensure isolation between the outer conductor of the coaxial cable and the elongate conductive member.

The snare base may be attached at the end of the sleeve, whereby the coaxial cable and the length of conductive material that forms the retractable loop may be movable (e.g. slidable) relative to the snare base. The snare base may thus comprises a cylindrical plug element at the distal end of the sleeve, wherein the plug element has a first passageway therethrough which provides the feed channel and a second passageway therethrough for conveying the coaxial cable.

The length of conductive material that forms the retractable loop may have a first end that is attached to a movement mechanism (e.g. push rod as explained below) for extended and retracting the retractable loop, and a second end that is attached (i.e. fixed) to the snare base.

In one embodiment, the snare base comprises a terminal cap fixed to the distal end of the sleeve. The second end of the length of conductive material that forms the retractable loop may be attached to an outer surface of the coaxial cable. If the coaxial cable is slidable within the sleeve, this arrangement means that the second end of the retractable loop can be moved within the sleeve. This may facilitate full retraction of the snare.

The retractable loop may be made from any suitable wire-like material, e.g. nitinol, nylon, metal wire or the like. Preferably the material has shape retaining properties so that it automatically adopts a loop configuration upon being released from a retracted configuration. Thus, the retractable loop may comprise a wire that extends beyond the distal end of the coaxial cable, the wire being arranged to naturally adopt a looped shape between two ends located at the distal end of the coaxial cable. The retractable loop may be adjustable to vary the length of wire between the two ends. The looped shape may be free from irregularities. In particular, the looped shape may not require a distal hump or nib such as those commonly found on conventional surgical snares to ensure that they retract in a predetermined manner. The invention may obviate the need for such a nib through the use of nitinol as the loop material, and/or through the use of the deployment mechanisms set forth herein. Omitting the distal nib may ensure that the snare provides a cleaner mechanical cut, which in turn provides a better en-bloc specimen for histological assessment and facilitates complete excision of tissue circled by the snare.

The retractable loop may be movable relative to the snare base, e.g. into and out of a storage channel formed in the sleeve surrounding the coaxial cable. Preferably the retractable loop is be movable relative to the coaxial cable. However, it may be possible for the retractable loop to be fixed relative to the coaxial cable and for retraction to be performed by moving a tubular cover relative to the coaxial cable over the loop.

A pull wire (or push rod) may be connected or formed integrally with the retractable loop. The pull wire may extend to the proximal end of the coaxial cable to enable the operator to deploy the snare. The pull wire may be connected to a slider mechanism (e.g. a manual slider mechanism) at the proximal end of the device. The pull wire may be conveyed from the proximal end to the distal end through a passageway in the sleeve. It is desirable for the translation between the length of movement of the slider at the proximal end and the opening and closing of the loop (or changes in diameter once it comes out of the end of the catheter or tube) to be consistent. A thin lubricious tube may be attached (e.g. glued) to the outer jacket of the coaxial cable to act as a guide for the pull wire (or pull wires). Alternatively, a very thin walled heat-shrinkable tube could be used to attach the guide tube to the coaxial cable. The guide tube preferably runs straight along the axis of the coaxial cable.

A multi-lumen tube may be inserted inside the structure to provide separate channels or spaces for the pull wire (or pull wires) and the coaxial cable. Alternatively, a single tube may be attached to the outer conductor of the coaxial cable to contain the pull wire to prevent the pull wire from becoming twisted around the coaxial cable.

The orientation of the loop may be related to the orientation of the passageway in the sleeve. Thus, the plane of the loop may be adjustable by rotating the sleeve. Preferably the sleeve is a braided cable capable of transferring torque. A hand grip for rotating the sleeve may be mounted on, e.g. clamped to, it at the proximal end.

Alternatively, the pull wire may also used to activate a screw mechanism that causes a linear to rotational translation, e.g. a lead screw arrangement, that can be used to rotate the loop. The same pull wire is used to open and close the loop or to push a loop made from a sprung material out of or into a catheter or tube to allow the loop to open and close.

The elongate conductive member may be retractable independently of the retractable loop. For example, the sleeve and the coaxial cable may be movable relative to other to move the elongate conductive member between a storage position in which it is surrounded by the elongate conductive member and a use position it which it protrudes from the sleeve. The retractable loop may be operable as a "cold" snare, i.e. a snare that operates without an accompanying microwave radiation field, when the elongate conductive member is in the storage position. In this arrangement, the snare may be used as a mechanically tissue capture and cutting tool. Tissue, e.g. a polyp stalk, may be encircled by the retractable loop when in an extended configuration. Upon retracting the loop, the encircled tissue may be forced against a distal surface of the snare base, whereupon the loop passes through the tissue to physically cut it. The distal surface of the snare base thus provides a reaction surface for the mechanical cutting action of the loop. The surface of the loop (or perhaps only the inner surface of the loop) may be roughened or sharpened to make this physical cutting action more effective. In some circumstances, use of the device as a "cold" snare may be preferable, as it may reduce the risk of delayed bleeding.

The first aspect of the invention may also be expressed as an electrosurgical apparatus comprising a microwave signal generator for outputting microwave frequency energy, and a surgical snare as described above connected to receive the microwave frequency energy and deliver it through the coaxial cable to be emitting as a microwave frequency field by the elongate conductive member.

According to a second aspect of the invention, there is provided a surgical snare comprising: a retractable loop for encircling an area containing biological tissue; a radiating structure arranged to radiate microwave frequency energy into the area encircled by the retractable loop; and a coaxial cable for conveying microwave frequency energy to the radiating structure, the coaxial cable comprising an inner conductor, an outer conductor surrounding and coaxial with the inner conductor, and a dielectric material separating the inner conductor and the outer conductor, wherein the radiating structure comprises a curved conductive portion partially bounding the area encircled by the retractable loop, the curved conductive portion being connected to the inner conductor of the coaxial cable and electrically insulated from the outer conductor of the coaxial cable to act as a radiating microwave monopole antenna. The second aspect differs from the first aspect in the nature of the radiating structure, which in this case is a curved conductive portion of the snare's loop, rather than an elongate element protruding into the loop. However, the curved conductive portion still acts as a radiating microwave antenna to deliver the microwave frequency energy into tissue held within the loop.

The curved conductive portion may extend between two ends, which may be spaced at equal distances from the point at which the inner conductor of the coaxial cable is connected to the curved conductive portion. The curved conductive portion may thus be symmetrically arranged at the distal end of the coaxial cable. Preferably, the electrical length between the ends of the curved conductive portion is $$\frac{(2n-1)\lambda_L}{4},$$

where $\lambda_L$ is the wavelength of the microwave frequency energy when propagating through the biological tissue, and n is a positive integer. Thus, the length of the curved conductive portion can be determined in the same way as the elongate conductive element of the first aspect. However, the structure of the second aspect not invasive. The length of the curved conductive portion may thus be longer that the elongate conductive element of the first aspect, e.g. 10 mm or more.

The curved conductive portion may comprise a pair of flexible prongs extending from the distal end of the coaxial cable. Each prong may be a wire or tube having a thickness or diameter selected such that it exhibits some intrinsic elasticity. The prongs may be symmetrically mounted with respect to the point of connection with the inner conductor of the coaxial cable (i.e. the feed point). The prongs may thus act to split the microwave frequency power received from the coaxial cable. The impedance of the prongs may be selected so that, when connected in parallel with the coaxial cable, they match the impedance of the coaxial cable, i.e. if the impedance of the lines that formed the prongs was 50Ω and the length of the prongs were made to be an odd multiple of a quarter wavelength at the frequency of choice, then each prong will be transformed to an impedance of 100Ω at the feed point to provide an overall parallel impedance of 50Ω, e.g. the same impedance as the characteristic impedance of the non-resonant co-axial line, to create the matched condition. The same principle can be applied for different load impedances.

The curved conductive portion may be movable relative to a tubular end cap between a stored configuration in which it is enclosed by the end cap and a deployed configuration in which it protrudes beyond a distal end of the end cap. The curved conductive portion may deform to fit inside the end cap. For example, the pair of prongs mentioned above may bend in towards each other. The outer diameter of the end cap may be less than 2.6 mm so that it can fit down the instrument channel of an endoscope. Thus, in the stored configuration, the curved conductive portion may be deformed to have a width of less than 2.5 mm.

The end cap may be slidable relative to the coaxial cable, e.g. via a pull wire that extends to the proximal end of the coaxial cable. As above, the coaxial cable may be encased in a sleeve, which may have a passageway formed therein for the pull wire. A multi-lumen tube may be inserted inside the main catheter or tube or sleeve.

The curved conductive portion may also act as a guide for the retractable loop. For example, the curved conductive element may comprise a hollow tubular section with an opening at one end thereof. The retractable loop, which is preferably formed from a non-conductive material such as nylon in this embodiment, may extend through the tubular section and through the opening. Having a hollow section of the curved conductive portion does not affect the propagation of the microwave frequency energy because the skin depth at such frequencies is small enough to require only a thin layer of conductive material, i.e. at 5.8 GHz, the skin depth or the depth into the material at which the electric field has reduced to 37% of its peak value, is in the order of micrometers ($1\times10^{-6}$ m) for good conductors, e.g. silver or gold.

The curved conductive portion may have a hollow tubular section through which the retractable loop extends at both ends thereof. However, in one embodiment, the retractable loop has a first end that is fixed (e.g. by laser welding) to one end of the curved conductive portion. The loop then passes into the opening of a hollow tubular portion on the other end of the curved conductive portion. The length of loop that protrudes from the opening may be adjustable, e.g. to adjust the area encircled by the snare. The snare may be asymmetric in this embodiment. Adjustment of the retractable loop may be via a pull wire that passes back to the proximal end of the coaxial cable. The curved conductive portion may have a second opening at a side facing away from the area enclosed by the loop.

Features of the first aspect expressed above may also be incorporated into the second aspect.

Similarly to the first aspect, the second aspect of the invention may also be expressed as an electrosurgical apparatus comprising a microwave signal generator for outputting microwave frequency energy, and a surgical snare as described above in relation to the second aspect connected to receive the microwave frequency energy and deliver it through the coaxial cable to be emitting as a microwave frequency field by the curved conductive portion.

According to a third aspect of the invention, there is provided a surgical snare comprising: a retractable loop for encircling an area containing biological tissue; a radiating structure arranged to radiate microwave frequency energy into the area encircled by the retractable loop; and a coaxial cable for conveying microwave frequency energy to the radiating structure, the coaxial cable comprising an inner conductor, an outer conductor surrounding and coaxial with the inner conductor, and a dielectric material separating the inner conductor and the outer conductor, wherein the radiating structure comprises a conductive portion formed in or on the retractable loop, the conductive portion being connected to receive microwave power from the coaxial cable and configured to radiate the received microwave frequency energy into the area encircled by the retractable loop.

The third aspect differs from the first and second aspect in that the radiating structure is actually part of the retractable loop itself. For example, part of the loop may be metallized, i.e. coating in a conductive material, and electrically connected to the inner conductor of the coaxial cable but electrically insulated from the outer conductor of the coaxial cable. The coaxial cable may include an insulating cap at its distal end. The inner conductor may protrude through the cap, but the outer conductor may be insulated by the cap from everything on the distal side of the cap. The protruding part of the inner conductor may be electrically connected to the conductive portion by crimping or the like.

To radiate efficiently into biological tissue, the electrical length of the conductive portion around the retractable loop may be $$\frac{(2n-1)\lambda_L}{4},$$

where $\lambda_L$ is the wavelength of the microwave frequency energy when propagating through the biological tissue, and n is a positive integer. The length of the conductive portion may be determined using the technique described above with reference to the first aspect of the invention.

In this aspect, the retractable loop may have a fixed end e.g. at the distal end of the coaxial cable, and an adjustable end, e.g. connected to a pull wire that may extend to a proximal end of the coaxial cable, where it is operable using a slider or the like. Similarly to the first and second aspects above, the snare may include a slidable end cap, although this is optional in this case because only the retractable loop may extend beyond the distal end of the coaxial cable.

The coaxial cable or sleeve may provide a torque-stable cable capable of transferring a rotational movement effected at the proximal end of the device to the retractable loop. Rotation of the loop enables the snare to be easily position over and around a polyp. In this aspect, the outer jacket of the co-axial cable may be semi-rigid or a tube (catheter) may be inserted over the outer jacket and form a tight fit.

Alternatively, rotation of the retractable loop may be achieved using a mechanism located at the distal end of the cable that transforms a linear movement of the pull wire or the cable to a rotational movement of the loop to control the angle of the loop with respect to the stalk or stem of the polyp to enable the loop to be in the correct orientation to allow the loop to go around the polyp stalk. This linear to rotational translation may also be used to control the opening and closing (diameter) of the loop or the amount of loop that protrudes from the snare base.

In one embodiment, the conductive portion may be a "leaky feeder", i.e. a length of coaxial cable that is shorted at its distal end and along which portions of the outer conductor are periodically removed to permit radiation therefrom. The portions of removed outer conductor may be separated by a distance of $(2n-1)\lambda_L/4$ where $\lambda_L$ is the wavelength of the microwave frequency energy when propagating through the biological tissue, and n is a positive integer.

Whilst the conductive portion may be part of the retractable loop itself, preferably the retractable loop comprises a wire made from insulating material that extends beyond the distal end of the coaxial cable, the wire being arranged to naturally adopt a looped shape between two ends located at the distal end of the coaxial cable. The conductive portion, which is connected to the inner conductor of the coaxial cable, may then be mounted on, e.g. bonded to or entwined with, the wire as it extends between the ends.

Features of the first aspect and second aspect expressed above may also be incorporated into the third aspect.

Similarly to the first and second aspects, the third aspect of the invention may also be expressed as an electrosurgical apparatus comprising a microwave signal generator for outputting microwave frequency energy, and a surgical snare as described above in relation to the third aspect connected to receive the microwave frequency energy and deliver it through the coaxial cable to be emitting as a microwave frequency field by the conductive portion.

In any of the aspects described above, the snare may include a fluid delivery channel for introducing fluid such as saline on or close to the treatment site, e.g. to assist with coagulation or to flush the area. The fluid delivery channel may be provided in the sleeve encasing the coaxial cable, or it may be provided in the inner conductor of the coaxial cable, e.g. by making it hollow.

The pull wire for the retractable loop is preferably may from an insulating material to avoid capacitive coupling with the coaxial cable as it extends through the passage in the sleeve.

BRIEF DESCRIPTION OF THE DRAWINGS

Embodiments of the invention are described in detail below with reference to the accompanying drawings, in which.

DETAILED DESCRIPTION; FURTHER OPTIONS AND PREFERENCES

Figure 1A:
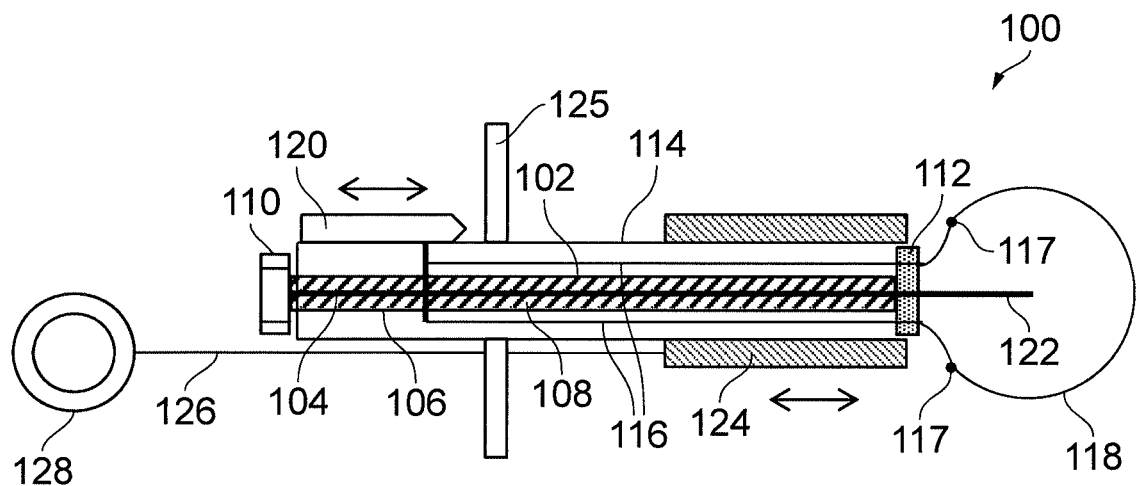
FIGS. 1A and 1B show a schematic cross-sectional view of a surgical snare that is a first embodiment of the invention, in a deployed and retracted position respectively.

FIG. 1A shows a cross-sectional view through a surgical snare 100 that is an embodiment of the invention. The drawing is schematic and not to scale. In particular, the relative length of the device is shortened substantially. In practice, the largest width (diameter) of the device is less than 2.6 mm in order to make it suitable for passing through the instrument channel of an endoscope. The total length of the device, meanwhile, may be 2 m or more.

The surgical snare 100 comprises a coaxial cable 102, comprising an inner conductor 104, an outer conductor 106 and a dielectric material 108 separating the inner conductor 104 from the outer conductor 106. A microwave connector 110 (e.g. a QMA connector or mounted at a proximal end of the coaxial cable 102 for connecting to a microwave signal generator (not shown). A snare base 112 (e.g. a disc of a suitable e.g. a low loss microwave ceramic, PTFE, PEEK, Nylon or the like, mounted at a distal end of the coaxial cable 102.

Figure 1B:
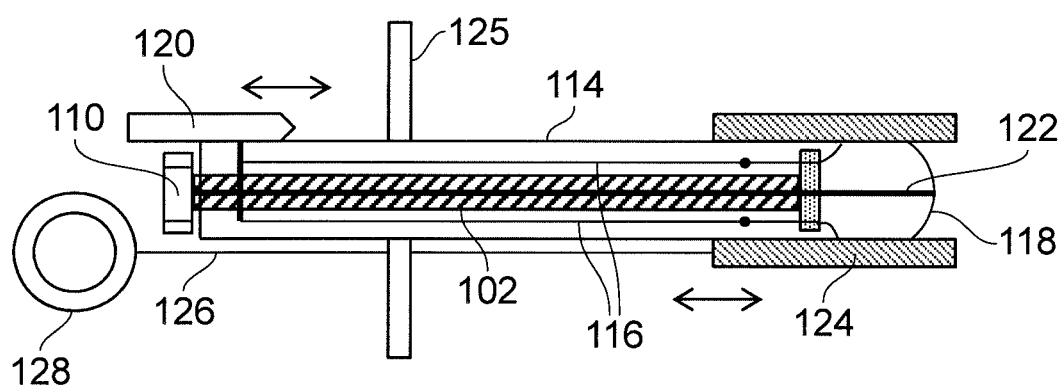

The coaxial cable 102 is encased in a sleeve 114. The sleeve 114 has a pair of passages for conveying a pair of pull wires 116 from the proximal end of the device to the distal end. Each pull wire 116 passes through the snare base 112 via a feed channel (i.e. a passageway formed in the snare base). The pair of pull wires 116 are each connected at their distal end to a respective end 117 of a length of wire 118 that forms a loop for the snare. The pair of pull wires 116 are each connected at their proximal end to a slider mechanism 120 which is movable relative to the sleeve 114. The slider mechanism 120 can be operated by the user to adjust the length of wire 118 that protrudes from the sleeve 114, thereby controlling the diameter of the loop formed by the length of wire 118 at the distal end of the device. The length of wire 118 may have a shape retaining property which allows it to deform in order to enter the passages in the sleeve, but recover its loop shape when drawn out again. FIG. 1A shows the loop in a fully deployed position. FIG. 1B shows the device with the loop partly withdrawn into the sleeve 114.

In this embodiment, the inner conductor 104 of the coaxial cable 102 protrudes through and beyond the snare base 112 to form an elongate conductive member 122. The function of the elongate conductive member 122 is as a microwave antenna (preferably a radiating monopole antenna) to radiate microwave frequency energy supplied to it through the coaxial cable 102. The elongate conductive member 122 may or may not penetrate the biological tissue that is encircled by the loop of the snare (e.g. the stem of a polyp), depending on its length. The elongate conductive member 122 includes a proximal portion that runs alongside the pull wires 116 in the snare base 112. Microwave energy delivered to the elongate conductive member 122 is coupled to set up a travelling wave in the pull wires 116 at this location, from where it is conveyed into and radiates from the wire loop 118. The strength of the radiated field is at a maximum at the distal end of the loop, where the travelling waves from each of the pull wires meet.

The microwave energy delivered to the elongate conductive member is radiated into the tissue, where it will promote coagulation and therefore assist in the removal of the biological tissue or prevent bleeding which would otherwise occur if mechanical action only was employed. It may be preferable to deliver microwave radiation continuously when a mechanical force is applied to the polyp stalk. Alternatively, the microwave source may be activated based on the measurement of a physical force, e.g. measured using a mechanical to electrical transducer, such as a piezoelectric transducer force sensor or the like.

The microwave energy may be delivered as a sequence of pulses or a burst of microwave energy, whereby the mechanical force follows or is embedded within the burst of microwave coagulation energy. For example, one activation profile may comprise applying 10 W of microwave power for 10 seconds, and applying the mechanical force for shorter periods within that 10 second time frame., i.e. the mechanical and microwave energy are delivered together and microwave energy is always applied, but mechanical energy is applied at intervals within the window of application of the microwave energy.

It may also be desirable to deliver the microwave energy based on the detection of a change in the reflected signal caused by a change in the impedance of the tissue that makes contact with the radiating monopole (or other) antenna, i.e. only deliver the microwave energy when the impedance of blood is detected. In addition, the delivery of the microwave energy may cease when a change of impedance is detected, i.e. the impedance of coagulated blood is detected. The measurement information may be magnitude only or magnitude and phase or phase only. To achieve this function effectively, the electrical length of the elongate conductive member 122 is determined based on a knowledge of the dielectric constant $\varepsilon_r$ of the biological tissue to be treated, the equivalent dielectric properties of the structure surrounding the elongate conductive member 122 in the snare base 112, and the frequency f of the microwave frequency energy that will be provided through the coaxial cable. This information is used to calculate a wavelength $\lambda_L$ of the microwave energy as it propagates through the biological tissue. The electrical length of the elongate conductive member 122 is set to be an odd number of quarter wavelengths, i.e.

$$\frac{(2n-1)\lambda_L}{4}, \text{ where } \lambda_L = \frac{c}{f\sqrt{\varepsilon_r}}$$

and c is the speed of light at the frequency of choice.

To avoid damaging the elongate conductive member 122 as the device is inserted along the instrument channel of an endoscope, a slidable tubular cover 124 is mounted at the distal end of the sleeve 114. A pull wire 126 extends from the tubular cover 124 to a handle 128 at the proximal end of the snare. The handle 128 may be operated by the user to slide the cover 124 over the elongate conductive member 122 (as shown in FIG. 1B). In use, the cover 124 is slid back over the sleeve 114 to expose the elongate conductive member 122.

The wire loop 118 may be rotated by turning a handle 125 that is attached to the sleeve 114. The sleeve may include a braided cable which facilitates accurate torque transfer to allow the rotation of the wire loop to be controlled precisely.

Figure 2A:
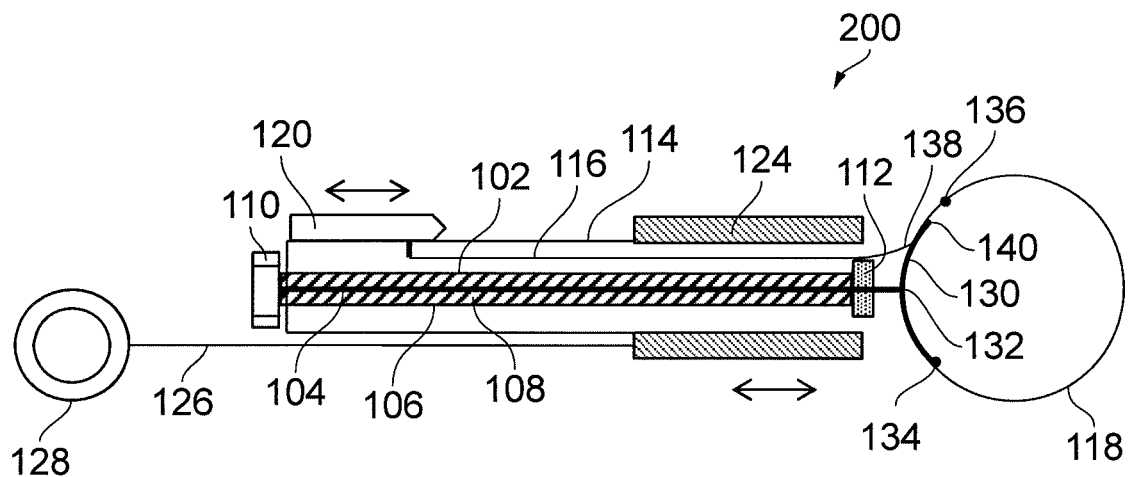
FIGS. 2A and 2B show a schematic cross-sectional view of a surgical snare that is a second embodiment of the invention, in a deployed and retracted position respectively.

FIG. 2A shows a cross-sectional view through a surgical snare 200 that is another embodiment of the invention. Similarly to FIGS. 1A and 1B, the drawing is schematic and not to scale. Features in common with FIGS. 1A and 1B are given the same reference numbers and are not described again. The handle 125 is omitted for clarity.

In FIG. 2A the inner conductor 104 of the coaxial cable 102 is connected to a curved conductive portion 130 which comprises a pair of curved prongs which extend symmetrically away from the feed point 132 at which they are connected to the inner conductor 104. Each prong may be a flexible elongate conductor, e.g. a wire or tube. In this embodiment, the length of wire 118 that forms a loop for the snare is fixed at one end to a distal end 134 of one of the prongs. The other end of the length of wire 118 is connected to the distal end 136 of a pull wire 116. The proximal end of the pull wire 116 is connected to the slider 120, which operates in the same manner as discussed above with reference to FIGS. 1A and 1B.

However, in this embodiment, the pull wire 116 and length of wire 118 forming the loop for the snare are arranged to pass through a guide passage formed in one of the prongs. Thus, upon exiting the passage in the sleeve 114, the pull wire 116 or wire 118 pass through a rear opening 138 on one of the prongs, through a hollow guide passage in that prong, to exit through a front opening 140 at the distal end of that prong.

The function of the curved conductive portion 130 is the same as the elongate conductive element 122 discussed above: it is a radiating microwave monopole antenna for radiating microwave frequency energy supplied to it through the coaxial cable 102. In use, the curved conductive portion 130 will contact the biological tissue that is encircled by the loop of the snare (e.g. the stem of a polyp). The microwave energy will therefore be radiated into the tissue, where it will promote coagulation and therefore assist in the removal of the biological tissue. To achieve this function effectively, the electrical length of the curved conductive portion 130 is therefore determined in a similar way to the elongate conductive element 122 discussed above, i.e. it is determined based on a knowledge of the dielectric constant $\varepsilon_r$ of the biological tissue to be treated and the frequency f of the microwave frequency energy that will be provided through the coaxial cable. This information is used to calculate a wavelength $\lambda_L$ of the microwave energy as it propagates through the biological tissue. The electrical length of the curved conductive member 130 is thus set to be an odd number of quarter wavelengths, i.e.

$$\frac{(2n-1)\lambda_L}{4}, \text{ where } \lambda_L = \frac{c}{f\sqrt{\varepsilon_r}}$$

and c is the speed of light.

Figure 2B:
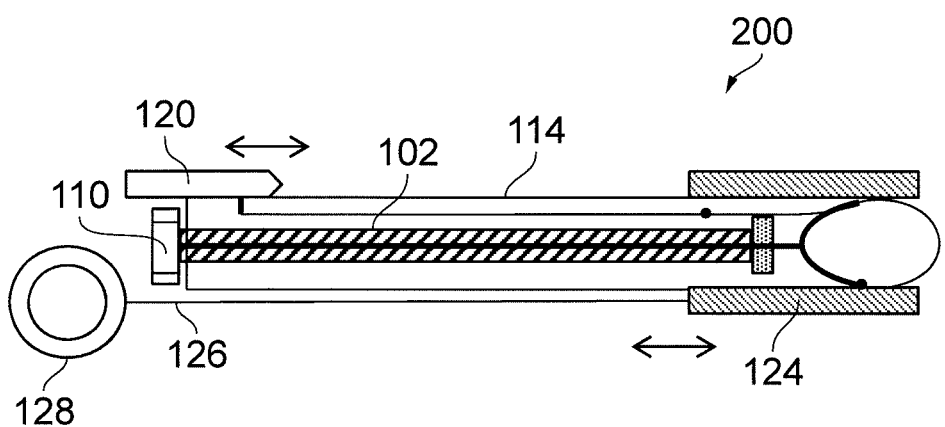

However, as the curved conductive portion 130 does not penetrate tissue, it can be made longer than the elongate conductive element 122. In order to fit down the instrument channel of an endoscope, the prongs of the curved conductive portion 130 preferably deform when the cover 124 is slid over them, as shown in FIG. 2B. The prongs may be resiliently deformable so that they regain their original position when the cover 124 is slid back over the sleeve 114.

Figure 3A:
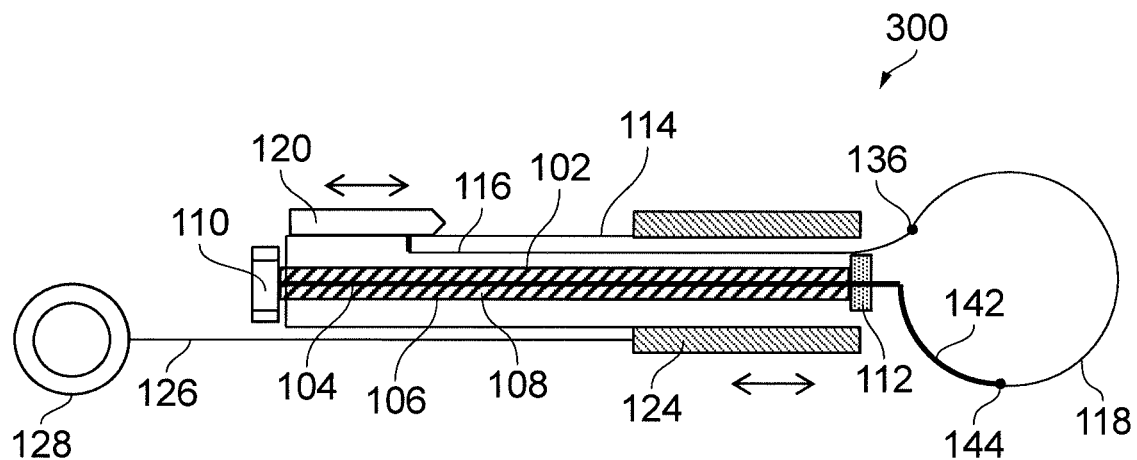
FIGS. 3A and 3B show a schematic cross-sectional view of a surgical snare that is a third embodiment of the invention, in a deployed and retracted position respectively.

FIG. 3A shows a cross-sectional view through a surgical snare 300 that is another embodiment of the invention. Similarly to FIGS. 1A and 1B, the drawing is schematic and not to scale. Features in common with FIGS. 1A and 1B are given the same reference numbers and are not described again.

In FIG. 3A the inner conductor 104 of the coaxial cable is connected to a conductive portion 142 which is mounted on the wire 118 that forms the loop for the snare. The wire 118 in this embodiment is made from a non-conductive material (e.g. nylon).

Similarly to the other embodiments discussed above, the function of the conductive portion 142 is the same as the elongate conductive element 122 is as a radiating microwave monopole antenna for radiating microwave frequency energy supplied to it through the coaxial cable 102. In use, the conductive portion 142 will contact the biological tissue that is encircled by the loop of the snare (e.g. the stem of a polyp). The microwave energy will therefore be radiated into the tissue, where it will promote coagulation and therefore assist in the removal of the biological tissue. To achieve this function effectively, the electrical length of the conductive portion 142 is therefore determined in a similar way to the elongate conductive element 122 discussed above, i.e. it is determined based on a knowledge of the dielectric constant $\varepsilon_r$ of the biological tissue to be treated and the frequency f of the microwave frequency energy that will be provided through the coaxial cable. This information is used to calculate a wavelength $\lambda_L$ of the microwave energy as it propagates through the biological tissue. The electrical length of the conductive member 142 is thus set to be an odd number of quarter wavelengths, i.e.

$$\frac{(2n-1)\lambda_L}{4}, \text{ where } \lambda_L = \frac{c}{f\sqrt{\varepsilon_r}}$$

and c is the speed of light. It should also be noted that the conductivity and the dielectric constant of the biological tissue are a function of the frequency of the microwave energy, and these parameters, together with the physical geometry of the antenna and the power lever (or energy delivery profile) determine the depth of penetration of the electric field into the tissue structure, e.g. polyp stem, mucosa, etc., which determines the profile of the focused heat.

Alternatively, however, the conductive member 142 may itself be a coaxial cable with an inner conductor electrically connected to the inner conductor 104 of the coaxial cable 102 and a ground outer conductor. The inner and outer conductors may be connected together at the distal end 144 of the conductive portion 142, e.g. where it connected to the wire 118. This structure may be made to radiate by removing periodically spaced sections of the outer conductor. The sections may be spaced by an odd number of quarter wavelengths, i.e.

$$\frac{(2n-1)\lambda_L}{4}.$$

This structure is also known as a 'leaky feed'.

In this embodiment, the length of wire 118 that forms a loop for the snare is fixed at one end to a distal end 144 of the conductive portion 132. The other end of the length of wire 118 is connected to the distal end 136 of a pull wire 116. The proximal end of the pull wire 116 is connected to the slider 120, which operates in the same manner as discussed above with reference to FIGS. 1A and 1B.

Figure 3B:
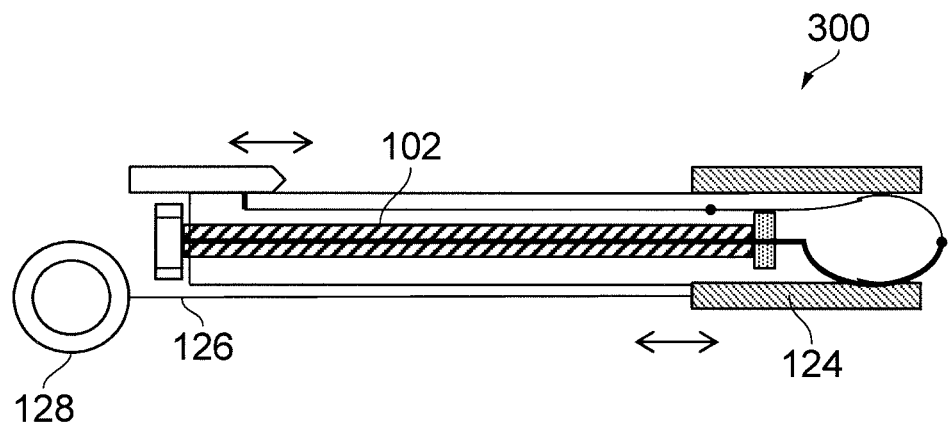

The conductive element 142 may be deformable in a manner similar to that shown in FIGS. 2A and 2B when the cover 124 is slid forward as shown in FIG. 3B. The conductive portion 142 or the wire 118 may be resiliently deformable so that they regain their original position when the cover 124 is slid back over the sleeve 114.

Figure 4:
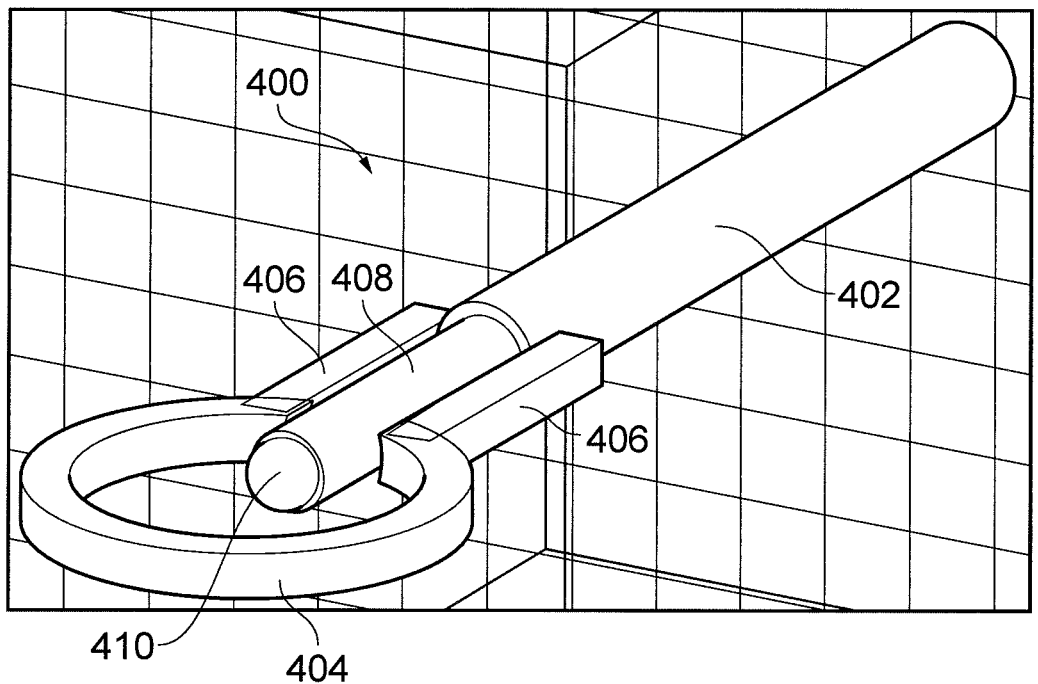
FIG. 4 is a perspective view of a model surgical snare used to simulate the microwave delivery performance of the invention.

FIG. 4 depicts a representative model 400 of a surgical snare according to the invention that was modeled using CST MICROWAVE STUDIO®, and the performance simulated as various modifications were made to the structure to improve the return loss (impedance match into tissue load model) and power density in the tissue.

In order to allow room for the mechanism to mechanically operate the snare, the coaxial cable 402 required to feed microwave energy down the endoscope channel is selected to have a diameter that is around 1.2 mm in diameter. Sucoform 47 (made by Huber+Suhner) is a suitable cable that is 1.2 mm in diameter and is flexible enough to allow full manipulation of the endoscope with the cable within its channel. Sucoform 86 cable, with an outside diameter of around 2.2 mm may also be a suitable candidate for implementing the microwave snare.

Figure 11:
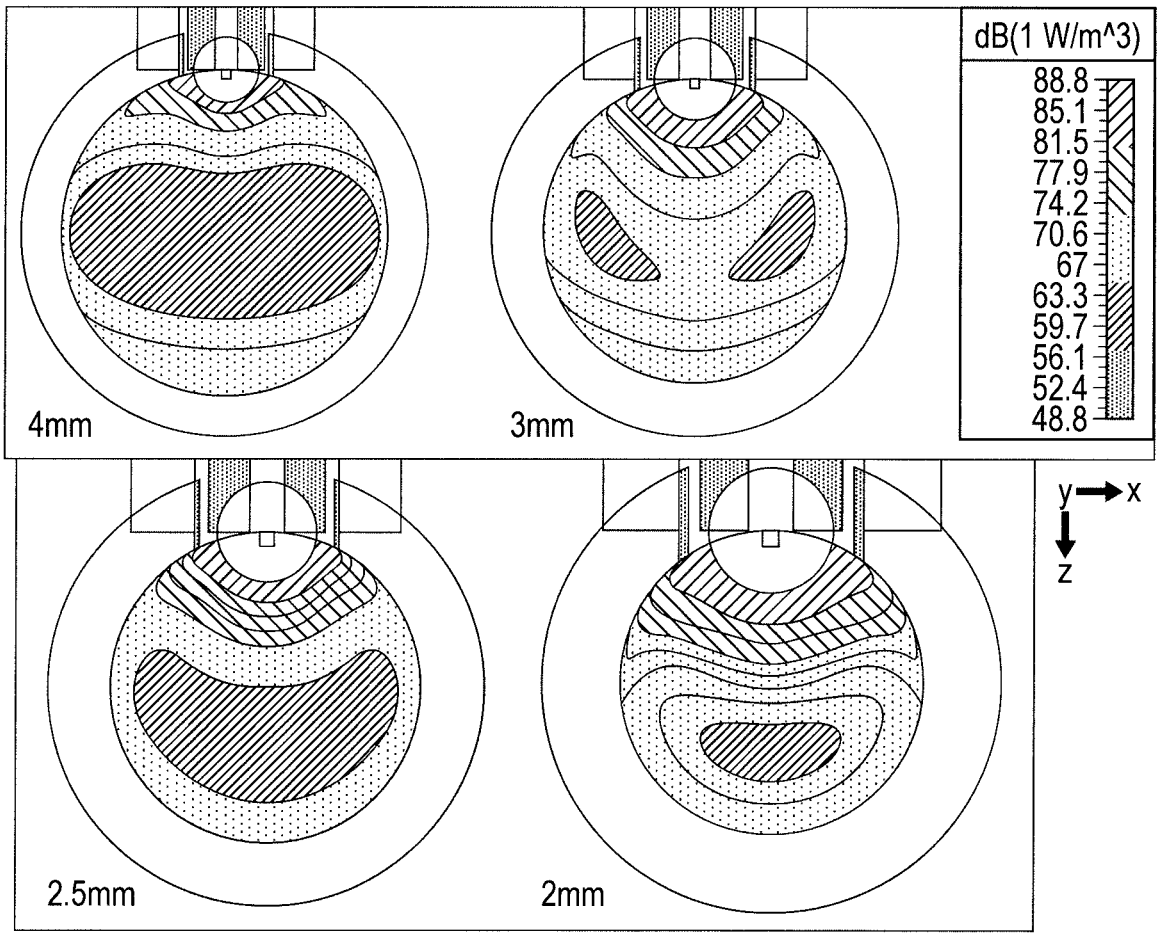
FIG. 11 shows four plan views of the model surgical snare of FIG. 8 showing power loss density into blood for four different loop diameters.

The retractable loop 404 of the snare was modeled as a circular loop of square cross section wire of thickness 0.5 mm. For most of the simulations the internal diameter of the loop was 3.6 mm. This implies that the length of the antenna that will radiate into the stalk of the polyp is around 11 mm. Referring to FIG. 11, the loop was filled with a cylinder of tissue which for most of the simulations was given the microwave properties of blood. The loop is connected to two wires 406 which run beside the outer conductor of the coaxial cable 402, and overlap it by one wire thickness. No further wire length was modeled. The inner conductor and dielectric covering 408 were extended from the end of the coaxial cable 402 to project into the loop, and the end of the center conductor was connected to a spherical metal dome 410.

The structure of FIG. 4 was the result of some preliminary modeling, during which it was found that the return loss could be improved by moving the loop further from the end of the coaxial cable, and extending the inner conductor and dielectric covering 408.

The power density inside the loop is higher if the end of the center conductor is exposed than if it is covered with dielectric. However, if the end of the center conductor is kept at its original radius the power density close to its end is extremely high. Thus, placing a conducting dome on the end of the center conductor increases the power density in the loop and results in less concentrated power close to the conductor.

Figure 5:
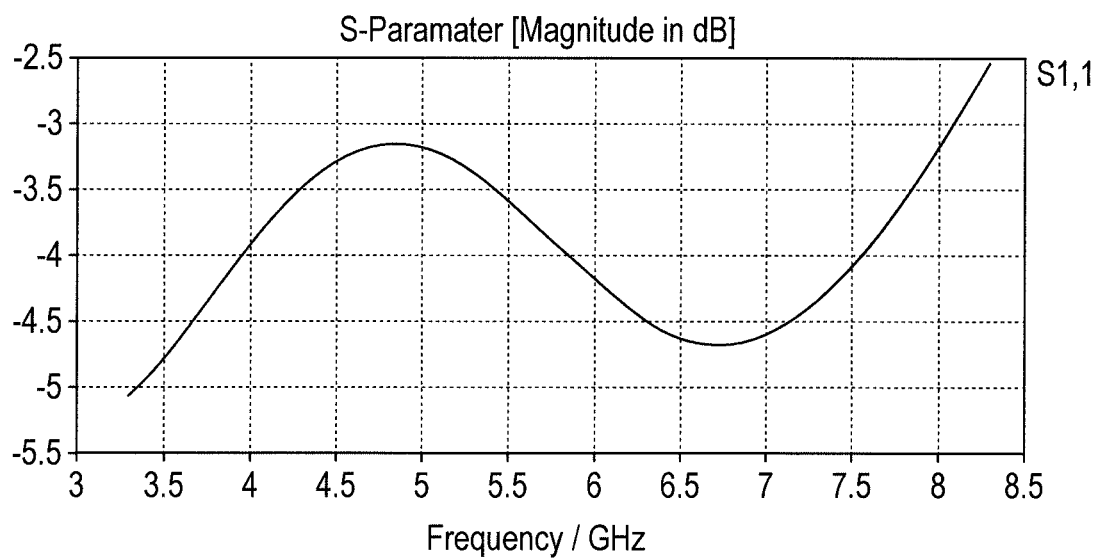
FIG. 5 is a graph showing return loss (impedance match) into blood for the model surgical snare shown in FIG. 4.

FIG. 5 shows the return loss for the configuration shown in FIG. 4, with a long cylinder of blood completely filling the loop. The dielectric properties of blood used in this simulation were as follows:

| | Conductivity [S/m] | Relative permittivity | Loss tangent | Wavelength [m] | Penetration depth [m] |
|---|---|---|---|---|---|
| Blood | 6.5057 | 52.539 | 0.38376 | 0.0070075 | 0.006019 |

Figure 6:
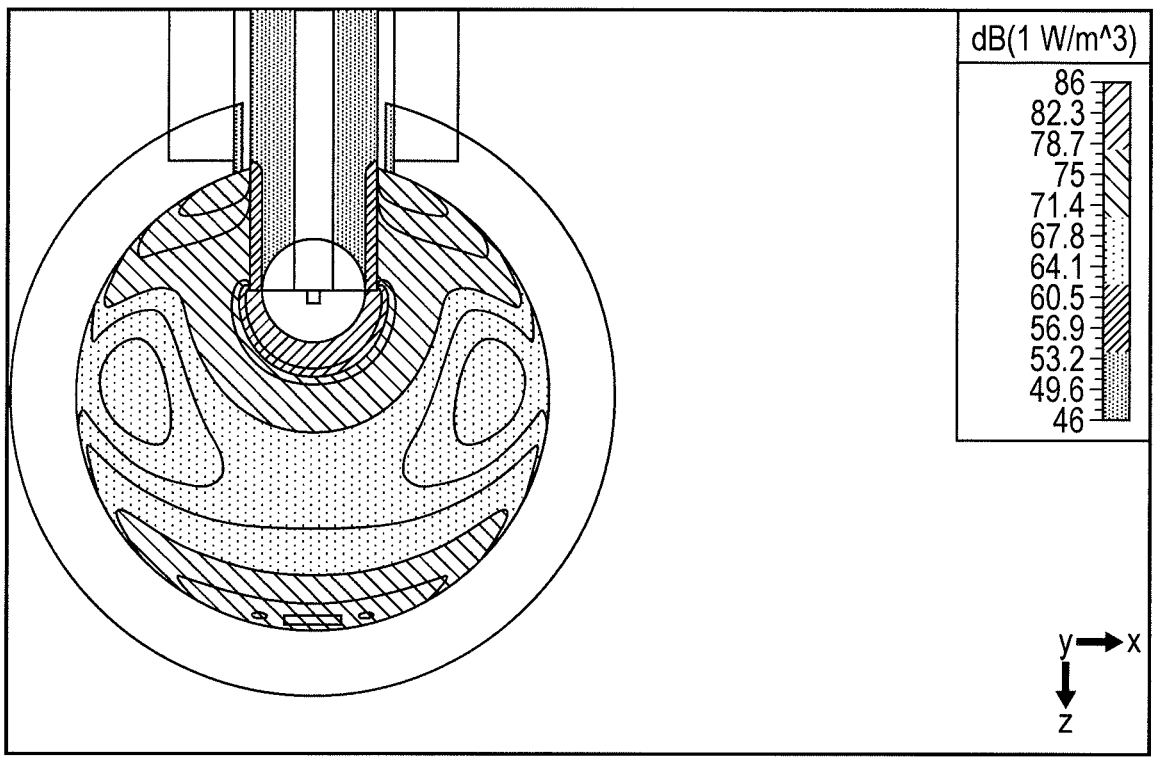
FIG. 6 is a plan view of the model surgical snare of FIG. 4 showing power loss density into blood.

FIG. 6 shows the power loss density in the plane of the loop. Here it has been assumed that the specific heat capacity of blood is about 4.2 J/(g·K), which is the specific heat capacity of water, and that the density of tissue is about 1 g/cm$^3$, which is the density of water, so that the volumetric heat capacity of tissue is about 4.2 J/(cm$^3$·K).

Most of the area surrounding by the loop has a power absorption of around 67 dBW/m$^3$, which is equivalent to 5 W/cm$^3$, for a 1 W input power. Thus, for a 10 W input power the power absorption would be 50 W/cm$^3$. This is enough to raise the temperature of the tissue in the loop by 12 Ks$^{-1}$. Close to the spherical dome the temperature rise will be considerably faster.

Figure 7:
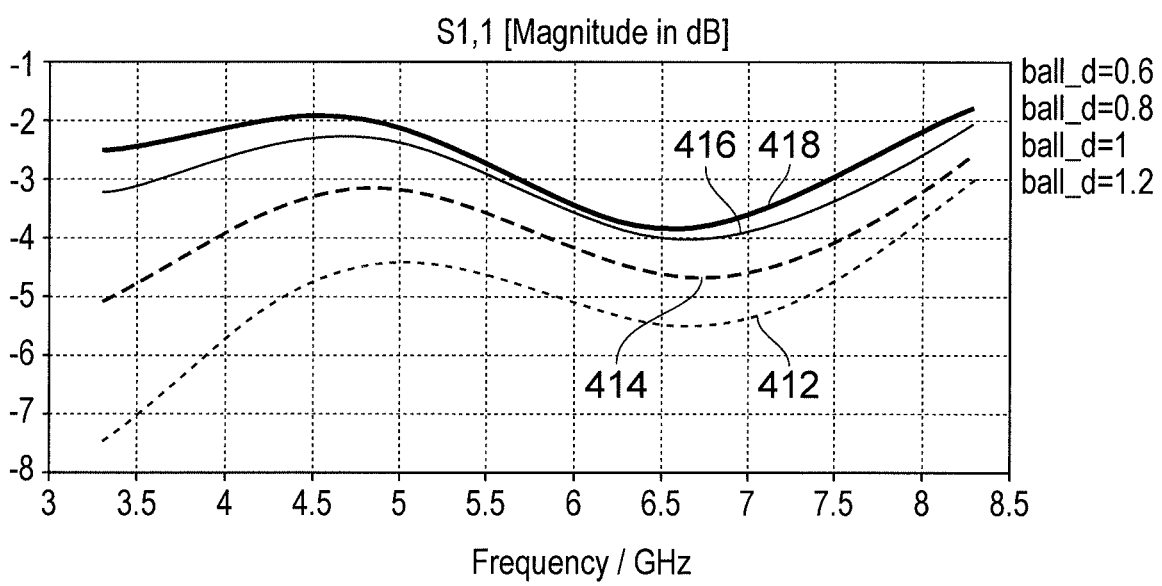
FIG. 7 is a graph showing return loss (impedance match) into blood for the model surgical snare of FIG. 4 with different tip diameters.

FIG. 7 illustrates the effect on the return loss of changing the diameter of the spherical tip. Line 412 represents a diameter of 0.6 mm. Line 414 represents a diameter of 0.8 mm. Line 416 represents a diameter of 1.0 mm. Line 418 represents a diameter of 1.2 mm. Smaller tip diameters give better return loss. However a larger diameter gives a better heat distribution and minimizes the risk of perforation. A diameter of 0.8 mm was chosen for further simulations.

Figure 8:
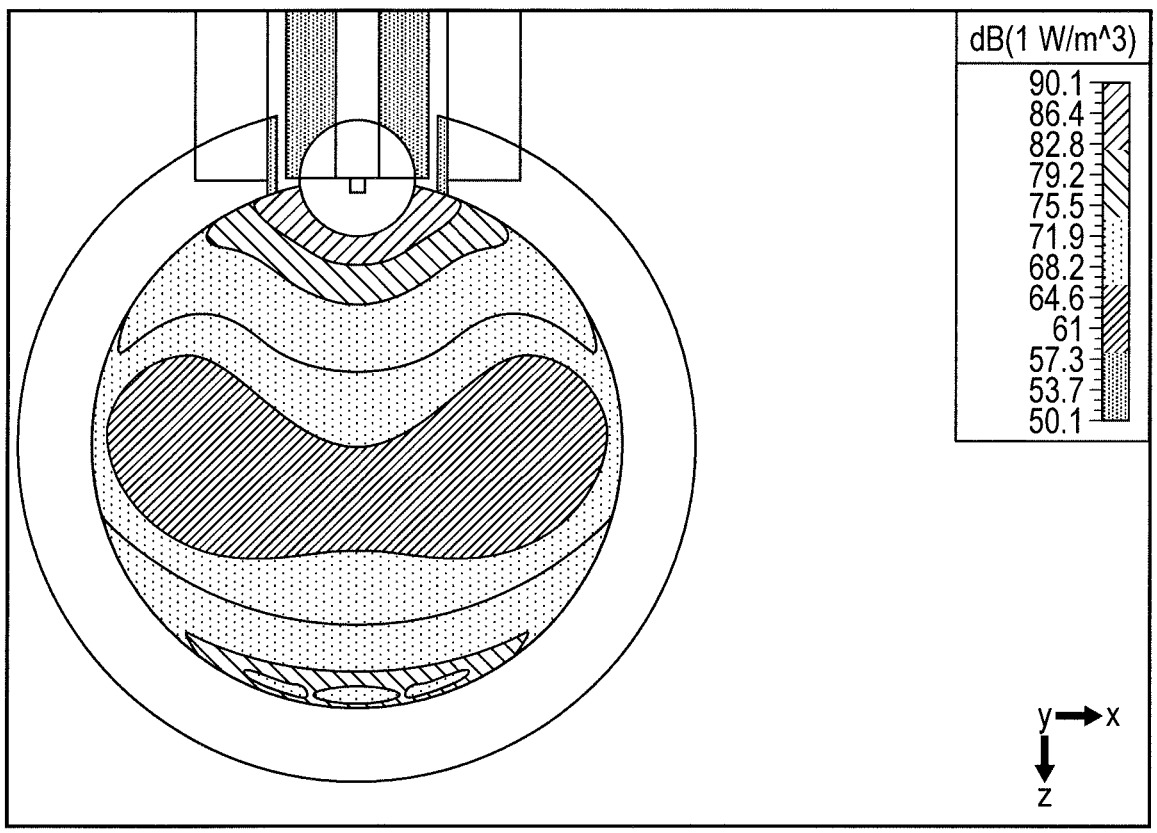
FIG. 8 is a plan view of the model surgical snare of FIG. 4 showing power loss density into blood with minimal protrusion of the probe into the area encircled by the retractable loop.
Figure 9:
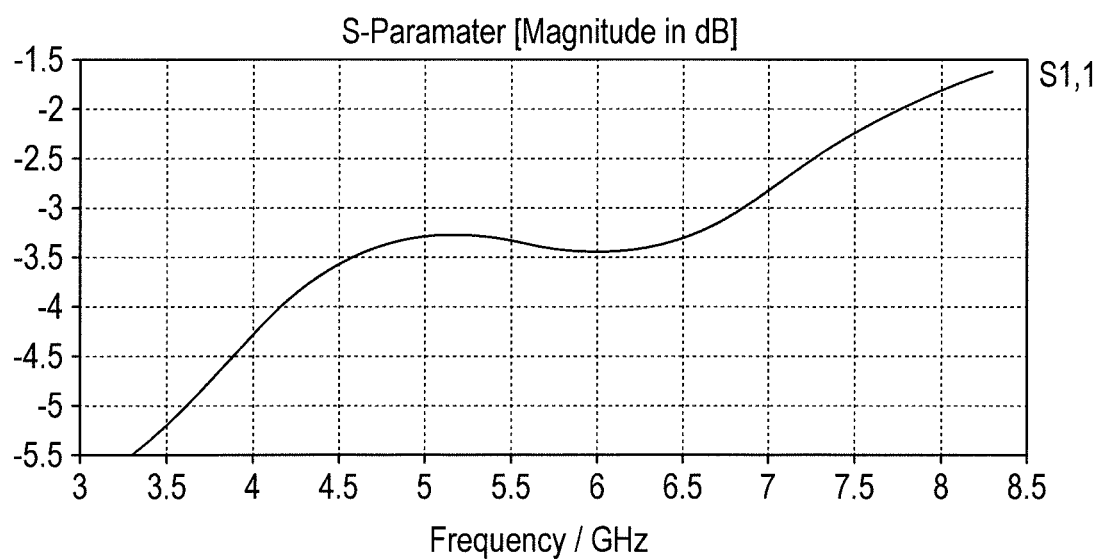
FIG. 9 is a graph showing return loss (impedance match) into blood for the model surgical snare of FIG. 8.

FIG. 8 shows the results of a simulation carried out on a structure where there is minimal protrusion of the spherical tip into the loop. In this arrangement it is intended for only the metal sphere to protrude into tissue captured by the loop. FIG. 8 shows the power loss density for the structure. It is slightly lower than with the fully protruding tip of FIG. 4. The central region of the loop in this arrangement has a power absorption level of around 64 dBW/m$^3$. FIG. 9 shows the return loss for the same structure.

Figure 10:
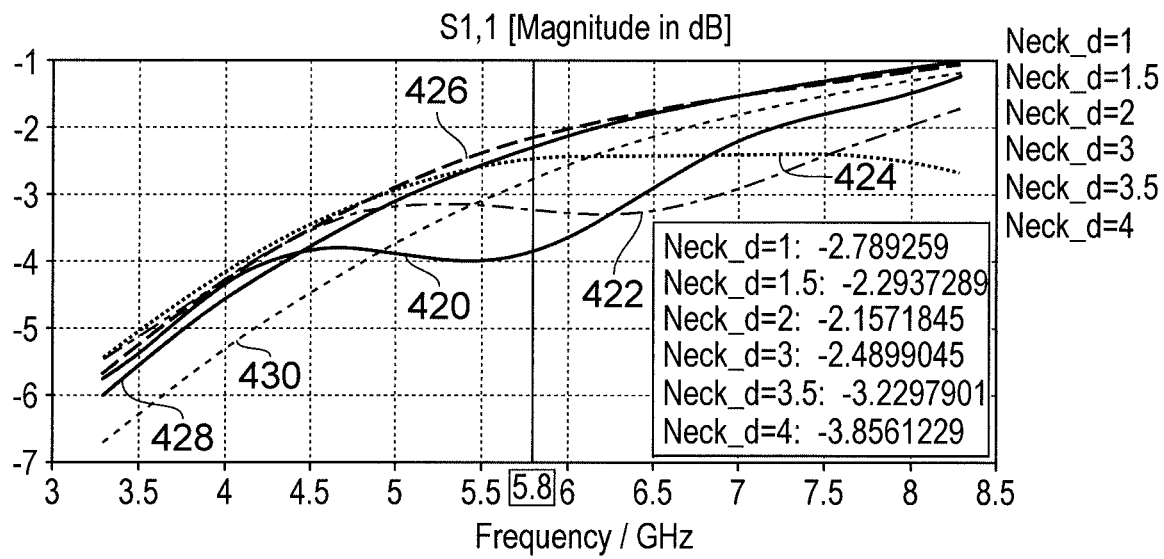
FIG. 10 is a graph showing return loss (impedance match) into blood for the model surgical snare of FIG. 8 with different loop diameters.

FIGS. 10 and 11 illustrate the effect of changing the diameter of the loop using the configuration of FIG. 8. FIG. 10 shows the return loss for six different diameters: 4 mm, 3.5 mm, 3 mm, 2 mm, 1.5 mm and 1 mm, represented by lines 420, 422, 424, 426, 428 and 430 respectively. At 5.8 GHz the return loss for each diameter is as follows:

| Loop diameter (mm) | Return loss (dB) |
| --- | --- |
| 1.0 | −2.789259 |
| 1.5 | −2.2937289 |
| 2.0 | −2.1571845 |
| 3.0 | −2.4899045 |
| 3.5 | −3.2297901 |
| 4.0 | −3.8561229 |

As the loop diameter reduces, at first the return loss worsens, but for diameters less than 2 mm the return loss begins to improve again (the higher the magnitude of the return loss, the better the impedance match into tissue or the more power will be delivered into the tissue).

FIG. 11 shows the power densities in the cylinder of blood enclosed in the loop for four loop diameters: 4 mm, 3 mm, 2.5 mm, 2 mm, and 1.5 mm. (The power density for a loop diameter of 3.6 mm is already shown in FIG. 8). These results show that the microwave power is adequate for loop diameters out to 4 mm and beyond. Given the stability of the profile, there is tolerance of loop shape too, i.e. the loop may take a large variety of shapes without disturbing the power absorption profile. For smaller diameters, even though the return loss get worse, the power density rises, particularly in the center of the loop, which means that the microwave heating becomes stronger as the loop tightens. Thus, the power density in the central region of the 4 mm loop is around 60 dBW/m$^3$, whereas in the central region of the 2 mm loop it is around 67 dBW/m$^3$.

The Sucoform 47 cable has an attenuation of about 3 dB/m at 5.8 GHz. This has an impact on the power that can be delivered to the end of the cable. The Sucoform 47 cable needs to be slightly longer than the endoscope channel, i.e. just over 2 m long, and so has an attenuation of about 7 dB. If the power available at the proximal end of the cable is 50 W (47 dBm), the maximum power than can be delivered at the distal end of the cable is about 10 W (40 dBm).

Figure 12A:
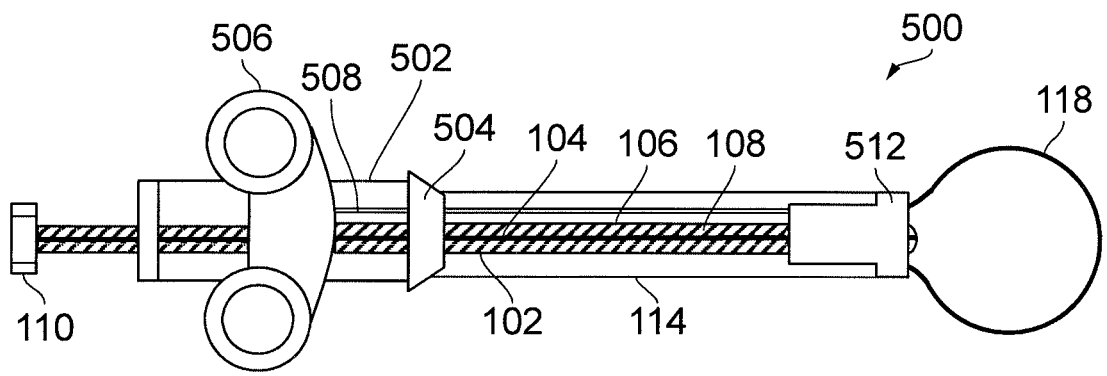
FIGS. 12A, 12B and 12C show a schematic cross-sectional view of a surgical snare that is a fourth embodiment of the invention, in a polyp capture position, a deployed antenna position and a retracted position respectively.

FIG. 12A shows a cross-sectional view through a surgical snare 500 that is another embodiment of the invention. Similarly to FIGS. 1A and 1B, the drawing is schematic and not to scale. Features in common with FIGS. 1A and 1B are given the same reference numbers and are not described again.

This embodiment differs from the arrangement shown in FIGS. 1A and 1B in that instead of having a sliding cover, the coaxial cable 102 is slidable within the sleeve 114 to cause the elongate conductive member 122 to protrude into the area encircled by the retractable loop 118. This embodiment therefore comprises a housing 502 at the proximal end of the device. The housing 502 has a tapered distal tip 504 which is attached, e.g. adhered or otherwise secured, to the proximal end of the sleeve 114. The housing 502 has a passageway therethrough for receiving the coaxial cable 102 in a manner that permits the coaxial cable 102 to slide relative to the housing 502 (and therefore the sleeve 114).

A handle 506 for operating the retractable loop 118 independently of the elongate conductive member 122 is slidably mounted on the housing 502 and connected to a proximal end of a push rod 508. The push rod 508 extends through the sleeve 114 and is attached at its distal end to a first end of the retractable loop 118.

This embodiment comprises a snare base 512 that is fixed, e.g. adhered or otherwise secured, to the distal end of the sleeve 114. As shown in the expanded cross-sectional view of FIG. 12B, the snare base 512 has two longitudinal passageways therethrough. A first passageway 514 is for conveying the push rod 508. The distal end 117 of the push rod 508 that is connected to the first end of the retractable loop 118 is located within the first passageway 514 in this view. A second passageway 516 is for conveying the coaxial cable 102. The snare base 512 also receives the second end 518 of the retractable loop 118. The second end 518 is attached to the snare base 512.

FIG. 12A shows the surgical snare 500 of this embodiment in a configuration where the elongate conductive member is retracted but the retractable loop 118 is extended. This may correspond to a polyp capture position, where the retractable loop is open to fit over a polyp.

Figure 12B:
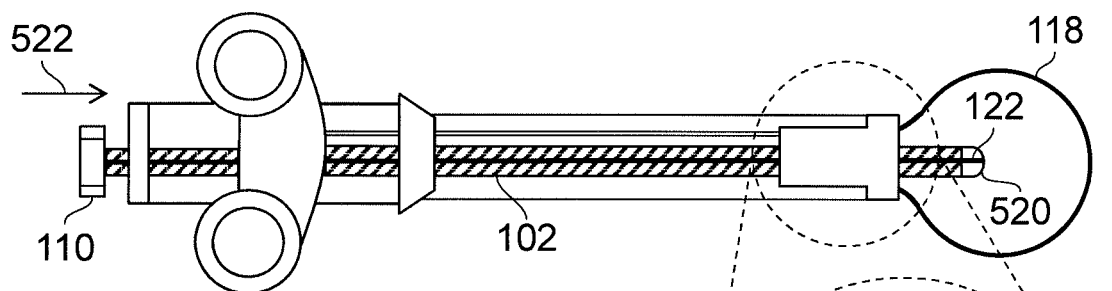

FIG. 12B shows the surgical snare 500 of this embodiment in a configuration where the elongate conductive member 122 is extended into the area encircled by the retractable loop 118. This may correspond to a deployed antenna position in which the elongate conductive member 122 may deliver microwave frequency energy into tissue captured within the retractable loop 118. To arrive in this configuration from the polyp capture configuration shown in FIG. 12A, the coaxial cable 102 is moved distally (to the right as shown in FIG. 12B by arrow 522). In this embodiment, the elongate conductive member 122 has a rounded conductive tip 520 mounted thereon. The rounded conductive tip 520 may be formed from silver wire wrapped around and soldered to elongate conductive member 122, i.e. to the protruding portion of the inner conductor 104.

Figure 12C:
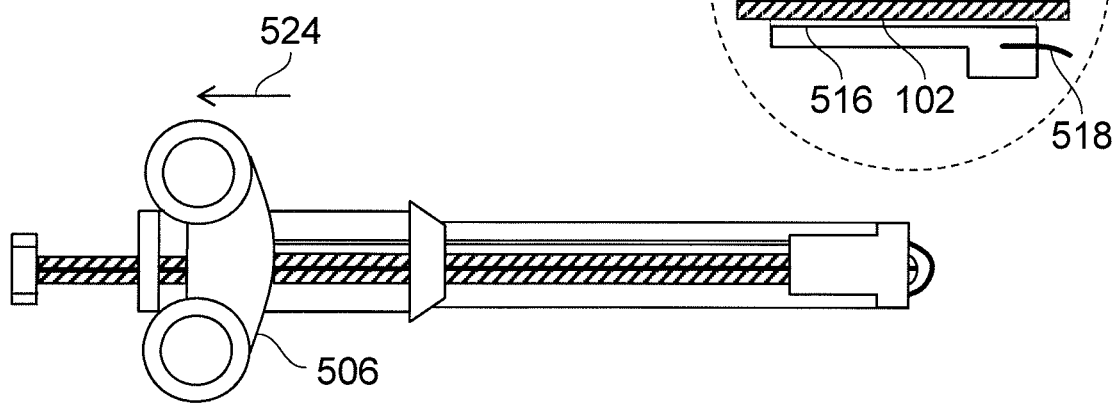

FIG. 12C shows the surgical snare 500 of this embodiment in a configuration where both the retractable loop 118 and the elongate conductive member 122 are fully retracted. This may correspond to a retracted position, e.g. for use when moving the device through the instrument channel of an endoscope. To arrive in this configuration from the polyp capture configuration shown in FIG. 12A, the handle 506 is moved proximally (to the left as shown in FIG. 12C by arrow 524).

The process of retraction may be used to assist cutting of biological tissue (e.g. a polyp stem) encircled by the retractable loop 118. The retractable loop may force the encircled tissue against the distal surface of the snare base 512, which thus forces a reaction surface to assist cutting. the distal surface of the snare base may be shaped to assist cutting, e.g. by being curved in a convex manner. The retractable loop 118 may have a roughened or sharpened surface (e.g. on the inside thereof) to assist cutting.

Figure 13A:
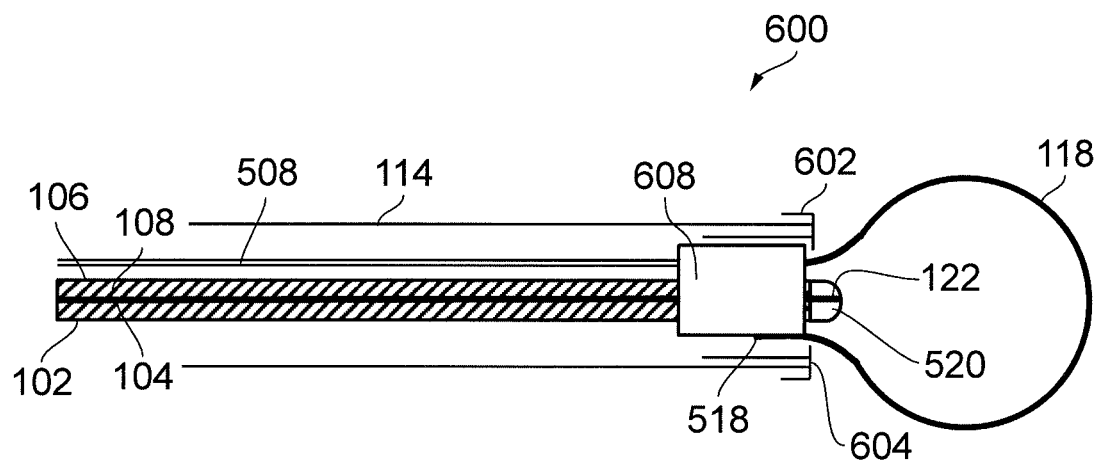
FIG. 13A shows a schematic cross-sectional view of a distal portion of a surgical snare that is a fifth embodiment of the invention.

FIG. 13A shows a schematic cross-sectional view of a distal portion of a surgical snare 600 that is another embodiment of the invention. This embodiment may use the same deployment mechanism (housing 502 and handle 506) as FIG. 12A, and so these feature are omitted for clarity. Features in common with FIGS. 1A and 1B and FIGS. 12A, 12B and 12C are given the same reference numbers and are not described again. Similarly to FIGS. 1A and 1B, the drawing is schematic and not to scale.

Similarly to the embodiment discussed with reference to FIGS. 12A, 12B and 12C above, in the embodiment of FIG. 13A the coaxial cable 102 is slidable with the sleeve 114 in order to extend and retract the elongate conductive member 122. Similarly, the retractable loop 118 is operated via the slidable push rod 508 in the same way as discussed above.

Figure 13B:
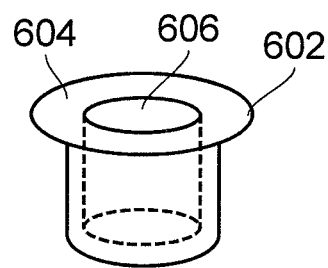
FIG. 13B is a perspective view of a cap used in the surgical snare shown in FIG. 13A.

However, the configuration of the snare base in FIG. 13A is different from FIGS. 12A, 12B and 12C. In this embodiment, the snare base comprises a cap 602 that is secured to the end of the sleeve 114. As shown in FIG. 13B, the cap 602 has a top hat shape, with an annular flange 604 that provides the distal surface thereof which mounted in use. The annular flange 604 may thus provide the reaction surface during mechanical cutting using the retractable loop 118. The cap has a passageway 606 therethrough for conveying the coaxial cable 102 and the push rod 508 or retractable loop 118.

Within the sleeve 114, a collar 608 is attached (e.g. adhered or soldered or otherwise affixed) to the outer surface (e.g. outer conductor 106) of the coaxial cable 102. The collar 608 thus moves with the coaxial cable 102 within the sleeve 114. The collar 608 has a larger diameter than the coaxial cable 102 and therefore leaves a space between its inner surface and the outer surface of the coaxial cable on a side of the coaxial cable that is opposite to the location at which the collar is attached to the coaxial cable. The push rod 508 passes through this space and is thus free to move relative to the coaxial cable 102.

The inner diameter of the flange 604 is smaller than the diameter of the collar 608 to act as a stop to limit the extent to which the elongate conductive member 122 can protrude out of the sleeve 114.

In this embodiment the other end 518 of the retractable loop 518 is attached (e.g. soldered) to the collar 608, e.g. to the outer surface of the collar 608. This means that the attachment point of the retractable loop 118 lies inside the sleeve 114, which may assist in complete retraction of the loop. Moreover, since the collar 608 is movable with the coaxial cable 102 within the sleeve 114, both ends of the retractable loop 118 are effectively movable within the sleeve, which can ensure that the loop is fully retractable.

The invention claimed is:

1. A surgical snare comprising:
a retractable loop of conductive material for encircling an area containing biological tissue;
a radiating structure arranged to radiate microwave frequency energy into the area encircled by the retractable loop;
a coaxial cable for conveying microwave frequency energy to the radiating structure, the coaxial cable comprising an inner conductor, an outer conductor surrounding and coaxial with the inner conductor, and a dielectric material separating the inner conductor and the outer conductor, and
a movement mechanism for extending and retracting the retractable loop; and
a sleeve surrounding the coaxial cable;
wherein the radiating structure comprises:
an elongate conductive member connected to the inner conductor of the coaxial cable and being electrically insulated from the outer conductor of the coaxial cable, and
a snare base at a distal end of the coaxial cable, the snare base having a feed channel for conveying a length of the conductive material that forms the retractable loop, the snare base being mounted at the distal end of the coaxial cable or being fixed to a distal end of the sleeve,
wherein the movement mechanism is operable to move the length of the conductive material relative to the snare base to retract the retractable loop relative to the coaxial cable towards the snare base, and
wherein the elongate conductive member comprises a distal portion that protrudes into the area encircled by the retractable loop to act as a radiating microwave monopole antenna, and a proximal portion that extends through the snare base alongside the feed channel.

2. A surgical snare according to claim 1, wherein the electrical length of the elongate conductive member is about $$\frac{(2n-1)\lambda_L}{4},$$

where $\lambda_L$ is a wavelength of the microwave frequency energy along the proximal portion of the elongate conductive member, and n is a positive integer.

3. A surgical snare according to claim 1, wherein the distal portion of the elongate conductive member is shaped to penetrate biological tissue.

4. A surgical snare according to claim 1, wherein the elongate conductive member is coated in a biocompatible material.

5. A surgical snare according to claim 1, wherein the snare base comprises an insulating disc.

6. A surgical snare according to claim 1, wherein the sleeve is configured for insertion through an instrument channel of an endoscope.

7. A surgical snare according to claim 6, wherein the sleeve comprises a rotatable braided cable to permit adjustment of an orientation of a plane of the retractable loop.

8. A surgical snare according to claim 1, wherein the retractable loop comprises a wire that extends beyond the distal end of the coaxial cable, the wire being arranged to naturally adopt a looped shape between two ends located at the distal end of the coaxial cable.

9. A surgical snare according to claim 8, wherein the retractable loop is adjustable to vary the length of wire between the two ends.

10. A surgical snare according to claim 1, wherein the elongate conductive member is retractable independently of the retractable loop.

11. A surgical snare according to claim 10 including a cover mounted at the distal end of the coaxial cable, and slidable between a covering position in which it overlaps the elongate conductive member and a retracted position in which the elongate conductive member protrudes therefrom.

12. A surgical snare according to claim 1, wherein the microwave frequency energy is in a range 1 GHz to 60 GHz.

13. Electrosurgical apparatus comprising:
a microwave signal generator for outputting microwave frequency energy having a frequency of 1 GHz or more, and a surgical snare according to claim 1 connected to receive the microwave frequency energy and deliver it through the coaxial cable to be emitted as a microwave frequency field by the elongate conductive member.

14. A surgical snare according to claim 1, wherein the movement mechanism comprises a slider mechanism and a wire or rod, wherein a distal end of the wire or rod is connected to, or formed integrally with, the retractable loop, and a proximal end of the wire or rod is connected to the slider mechanism, and wherein operation of the slider mechanism causes the wire or rod to retract or extend the retractable loop.

15. A surgical snare according to claim 6, wherein the movement mechanism is operable to retract the retractable loop into a storage channel formed between the sleeve and the coaxial cable.

16. A surgical snare comprising:
- a retractable loop of conductive material for encircling an area containing biological tissue;
- a radiating structure arranged to radiate microwave frequency energy into the area encircled by the retractable loop;
- a coaxial cable for conveying microwave frequency energy to the radiating structure, the coaxial cable comprising an inner conductor, an outer conductor surrounding and coaxial with the inner conductor, and a dielectric material separating the inner conductor and the outer conductor; and
- a sleeve surrounding the coaxial cable,
- wherein the radiating structure comprises:
- an elongate conductive member connected to the inner conductor of the coaxial cable and being electrically insulated from the outer conductor of the coaxial cable, and
- a snare base at a distal end of the coaxial cable, the snare base having a feed channel for conveying a length of the conductive material that forms the retractable loop, the snare base being mounted at the distal end of the coaxial cable,
- wherein the length of the conductive material is movable relative to the snare base whereby the retractable loop is retractable relative to the coaxial cable towards the snare base and into a storage channel formed between the sleeve and the coaxial cable, and
- wherein the elongate conductive member comprises a distal portion that protrudes into the area encircled by the retractable loop to act as a radiating microwave monopole antenna, and a proximal portion that extends through the snare base alongside the feed channel.

* * * * *